US009869662B2

(12) United States Patent
Kageyama (10) Patent No.: US 9,869,662 B2
(45) Date of Patent: Jan. 16, 2018

(54) CHROMATOGRAPH/MASS SPECTROMETER DATA PROCESSING DEVICE (71) Applicant: SHIMADZU CORPORATION, Kyoto-shi, Kyoto (JP)

(72) Inventor: Tetsuya Kageyama, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 505 days.

(21) Appl. No.: 14/309,039

(22) Filed: Jun. 19, 2014

(65) Prior Publication Data

US 2015/0369782 A1 Dec. 24, 2015

(51) Int. Cl.
G01N 30/72 (2006.01)
H01J 49/26 (2006.01)
G01N 30/86 (2006.01)
H01J 49/00 (2006.01)

(52) U.S. Cl.
CPC ......... *G01N 30/86* (2013.01); *G01N 30/7266* (2013.01); *H01J 49/0036* (2013.01); *G01N 30/72* (2013.01)

(58) Field of Classification Search
CPC .. G01N 30/72; G01N 30/7233; G01N 27/622; H01J 49/0036; H01J 49/26
See application file for complete search history.

(56) References Cited

U.S. PATENT DOCUMENTS

| 5,130,538 A | 7/1992 | Fenn et al. | |
| 5,900,628 A * | 5/1999 | Ishihara | H01J 49/0036 250/282 |
| 2007/0284520 A1* | 12/2007 | Yamamoto | H01J 49/0009 250/282 |
| 2012/0306883 A1* | 12/2012 | Yoshioka | G01N 30/86 345/440 |

FOREIGN PATENT DOCUMENTS

| JP | H08-334493 | 12/1996 |
| JP | 2011-242255 | 12/2011 |

OTHER PUBLICATIONS

Machine translation of JP H8-334493, downloaded Sep. 23, 2016.*
Japanese Office Action dated Jan. 13, 2015 in Japanese Patent Application No. 2011-278341.

* cited by examiner

*Primary Examiner* — Jan Ludlow
(74) *Attorney, Agent, or Firm* — Sughrue Mion, PLLC

(57) ABSTRACT

If multiple polyvalent ion peak candidates with different valences surmised to be derived from the target compound have been obtained, a mass chromatogram in the vicinity of the retention time of the target compound at the mass-charge ratio m/z of each polyvalent ion peak candidate is generated, and these are overlaid and displayed on the display screen. If the polyvalent ions are derived from the same compound, peaks of similar shape having a peak top near the retention time should appear in multiple mass chromatograms. Therefore, the user can check the displayed mass chromatograms (Continued)

(a) Likelihood that polyvalent ions are derived from the same compound is high (b) Likelihood that polyvalent ions are derived from the same compound is low and easily determine whether they reflect a combination of polyvalent ions derived from the target compound (a) or not (b).

4 Claims, 5 Drawing Sheets

CHROMATOGRAPH/MASS SPECTROMETER DATA PROCESSING DEVICE

This application incorporates herein by reference Japanese Patent Publication No. JP 2013-130411, published Jul. 4, 2013, to the same inventor.

TECHNICAL FIELD

The present invention relates to a data processing device which analyzes and processes data captured by a chromatograph/mass spectrometer, such as a liquid chromatograph/mass spectrometer (LC/MS); more specifically, the invention relates to a data processing device suitable for determining the presence or absence of polyvalent ions derived from a target compound based on data detected by a quadrupole mass spectrometer.

BACKGROUND ART

An atmospheric pressure ionization interface is used in order to ionize and perform mass analysis of a liquid sample or of analysis target components in a solution separated into components by a liquid chromatograph. Known typical atmospheric pressure ionization methods include electrospray ionization (ESI) and atmospheric pressure chemical ionization (APCI). Generally, this sort of atmospheric pressure ionization interface is often used in combination with a quadrupole mass spectrometer, ion trap mass spectrometer or time-of-flight mass spectrometer.

An atmospheric pressure ionization interface, particularly an ESI interface, has the characteristic of readily generating polyvalent ions having multiple charges in the process of ionizing a compound. Polyvalent ions, depending on the valence, have a smaller mass-charge ratio m/z than the molecular weight of the original compound, and thus have the advantage of making it possible to relatively lower the mass-charge ratio range of ions constituting the target of analysis. In particular, when analyzing high molecular weight compounds such as proteins and peptides, the mass-charge ratio of a monovalent ion may exceed the measurable range of a mass spectrometer, and using polyvalent ions makes it possible to keep the mass-charge ratio within the measurable range of the mass spectrometer. Due to this fact, mass analysis using polyvalent ions is highly effective for identifying high molecular weight compounds.

When a high molecular weight compound is ionized with an ESI ion source to perform mass analysis, peaks derived from ions with various valences appear on the mass spectrum (for example, see FIG. 1 of Non-patent Literature 2). When computational processing is performed by a technique called deconvolution on this sort of mass spectrum in which multiple polyvalent ion peaks are observed, a neutral mass spectrum is determined (for example, see FIG. 2 of Non-patent Literature 2), and based on this, the molecular weight of the target compound is obtained (see Patent Literature 1, Non-patent Literature 1, etc.).

The above-described conventional technique using deconvolution is useful when multiple (normally, about 10 or more) polyvalent ion peaks with different valences derived from the target compound are observed on the mass spectrum, and make it possible to determine molecular weight with adequate certainty. However, when only two or three polyvalent ion peaks are present on the mass spectrum, a technique using deconvolution cannot be said to be particularly effective. The reason for this is that, assuming M is the molecular weight corresponding to a polyvalent ion on the mass spectrum, i.e. the molecular weight of the compound, n is the valence of the ion, H is the molecular weight of a proton, and m is the observed ion mass/charge ratio m/z, if only two to three peaks corresponding to the following formula (1) are present, there is the possibility that those peaks will not be derived from the target compound but will rather be accidental matches.

$$M = n(m+H) \quad (1)$$

Furthermore, especially when the intensity of some of the ion peaks is low, it is difficult to distinguish them from noise peaks, etc., and it is rather difficult to judge based on the mass spectrum whether or not those multiple ion peaks are derived from the same target compound.

PRIOR ART LITERATURES (Patent literature 1) U.S. Pat. No. 5,130,538

NON-PATENT LITERATURES (Non-patent Literature 1) "(Technical classification) 2-2-3-1 General mass analysis technology/Ionic species/Attribution and identification/Polyvalent ions (Technical title) 2-2-3-1-1 Polyvalent ions", (online), Japan Patent Office, (Retrieved Nov. 17, 2011), Internet <URL: http://www.jpo.go.jp/shiryou/s_sonota/hyoujun_gijutsu/mass/2-2-3.pdf>

(Non-patent Literature 2) "Shimadzu Application News No. C55 Analysis of proteins and peptides using LC-MS", (online), Shimadzu Corporation, (Retrieved Nov. 17, 2011), Internet <URL: http://www.imtakt.com/jp/Support/UserReport/Shimadzu/LCMS/c55-CD0peptide.pdf>

SUMMARY OF THE INVENTION

The present invention was made to resolve the aforementioned problem, its purpose being to provide a chromatograph/mass spectrometer data processing device which, even when there are few types of polyvalent ions generated from the target compound, is able to eliminate the effects of accidentally matching unwanted peaks and can, for example, generate a high precision neutral mass spectrum for the target compound or determine the molecular weight of the target compound with high precision and can rapidly determine the presence or absence of polyvalent ions derived from the target compound based on the detected data.

A first aspect of the invention, made to resolve the above problem, is a chromatograph/mass spectrometer data processing device which analyzes and processes data on polyvalent ions derived from a target compound and captured by a chromatograph/mass spectrometer, such as LC/MS, characterized in that it comprises:

a) a polyvalent ion candidate extractor which finds one or more candidate polyvalent ion peak combinations derived from the target compound by extracting multiple polyvalent ion peak candidates of different valence surmised to be derived from the same compound on a mass spectrum obtained in the vicinity of the retention time of the target compound;

b) a mass chromatogram generator which generates a mass chromatogram at least in a time range in the vicinity of the retention time of said target compound for each of the multiple polyvalent ion peak candidates contained in the candidate combinations determined by said polyvalent ion candidate extractor; and c) a display which displays, on the same screen, multiple mass chromatograms for multiple polyvalent ion peak candidates contained in one candidate combination, generated by said mass chromatogram generator.

Furthermore, a second aspect of the invention made to resolve the above problem is a chromatograph/mass spectrometer data processing device which analyzes and processes data on polyvalent ions derived from a target compound and captured by a chromatograph/mass spectrometer, such as LC/MS, characterized in that it comprises:

a) a polyvalent ion candidate extractor which finds one or more candidate polyvalent ion peak combinations derived from the target compound by extracting multiple polyvalent ion peak candidates of different valence surmised to be derived from the same compound on a mass spectrum obtained in the vicinity of the retention time of the target compound;

b) a mass chromatogram generator which generates a mass chromatogram at least in a time range in the vicinity of the retention time of said target compound for each of the multiple polyvalent ion peak candidates contained in the candidate combinations determined by said polyvalent ion candidate extractor; and c) a candidate determination unit which determines whether or not each polyvalent ion peak candidate is a polyvalent ion peak derived from the target compound based on multiple mass chromatograms for multiple polyvalent ion peak candidates contained in one candidate combination, generated by said mass chromatogram generator.

If a mass chromatogram is generated for each of a plurality of polyvalent ion species of different valences derived from the same compound, in each of them, a chromatogram peak should appear in the vicinity of the time when the target compound appears (i.e. the retention time). Furthermore, the chromatogram peak shapes should be similar to each other. By contrast, if a peak derived from another compound or noise should be accidentally present at the position (mass-charge ratio) where a polyvalent ion peak appears on the mass spectrum, even if a mass spectrogram is generated for that mass-charge ratio, a chromatogram peak should not appear in the vicinity of the retention time of the target compound. This fact is made use of in the chromatograph/mass spectrometer data processing device of the first and second inventions to evaluate if a polyvalent ion peak candidate obtained from the mass spectrum is derived from the target compound. In the first invention, a mass chromatogram corresponding to the polyvalent ion peak candidates is displayed, thereby providing an environment which allows the user to select the appropriate candidate combination (i.e. the one most likely to be a polyvalent ion derived from the target compound) through visual inspection or the like. Furthermore, in the second aspect of the invention, instead of having the user himself make the determination, a candidate determination unit automatically evaluates the mass chromatogram and selects the appropriate candidate combination.

In the chromatograph/mass spectrometer data processing device according to the first and second aspects of the invention, the polyvalent ion candidate extractor, for example, assumes a certain molecular weight and extracts multiple peaks corresponding to the aforementioned formula (1) as polyvalent ion peak candidates from the mass spectrum in the vicinity of the retention time of the target compound. If the molecular weight of the target compound is largely known, one can delimit a predetermined molecular weight range centered on that known molecular weight with formula (1), and search for polyvalent ion peak candidates by changing the valence within a predetermined tolerance. Furthermore, if the molecular weight of the compound is unknown, the user can set the molecular weight range and valence range which the compound can take on, based on technical common knowledge, and thus the polyvalent ion peak candidates can be searched within the set range. One or more candidate combinations containing a plurality of polyvalent ion peak candidates of different valence derived from the same compound (i.e. for the same molecular weight) are then determined. Generally, there will be a plurality of such candidate combinations.

The mass chromatogram generator generates a mass chromatogram for the multiple polyvalent ion peaks contained in the candidate combination determined from the mass spectrum, for example, in a predetermined time range in the vicinity of the retention time of the target compound. Furthermore, in the first invention, the display displays multiple mass chromatograms for the multiple polyvalent ion peak candidates contained in a single candidate combination on the same screen. This allows the user to easily visually compare the peak shapes of the mass chromatograms of the polyvalent ion candidates appearing near the retention time of the target compound and simply judge whether these can be viewed as polyvalent ions derived from the same compound. Moreover, in the second invention, the candidate determination unit, for example, checks for the presence of chromatogram peaks in the vicinity of the retention time of the target compound on the mass chromatogram of polyvalent ion candidates, and if the peak shapes are similar, determines that there is a high probability that the polyvalent ion peaks contained in that candidate combination are true polyvalent ion peaks derived from the target compound. In this way, if multiple polyvalent ion peak combinations derived from the target compound are found, it is possible based thereon to generate a neutral spectrum for the target compound and to find the precise molecular weight.

As discussed above, if the multiple polyvalent ion peak candidates contained in a single candidate combination are all true polyvalent ion peaks, the reliability of that combination can be considered to be high. However, if the intensities of the multiple polyvalent ion peak candidates contained in a single candidate combination are all low, the possibility of an accidental match by peaks not derived from the target compound cannot be ruled out.

Thus, as a preferable mode for the chromatograph/mass spectrometer data processing device of the first and second inventions, the aforesaid polyvalent ion candidate extractor can be configured to discard or select a candidate combination on the condition that it contains at least one peak with a relatively large signal intensity on the mass spectrum obtained in the vicinity of the retention time of the target compound.

It is thus possible to eliminate at least some of the polyvalent ion peaks due to an accidental match of mass-charge ratio due to noise or the like, thus making it possible to reduce the number of candidate combinations and lessen the burden of evaluation work on the user. Alternatively, it is possible to increase the precision of automatic selection of the appropriate combination.

EFFECT OF THE INVENTION

With the chromatograph/mass spectrometer data processing device of aspects of the present invention, even in cases where two or three polyvalent ions derived from a target compound can be observed, it becomes possible to quickly and reliably determine the presence of polyvalent ions and to generate a high precision neutral mass spectrum and find the molecular weight of the target compound with high precision.

DETAILED DESCRIPTION OF THE EXEMPLARY EMBODIMENTS

Figure 1:
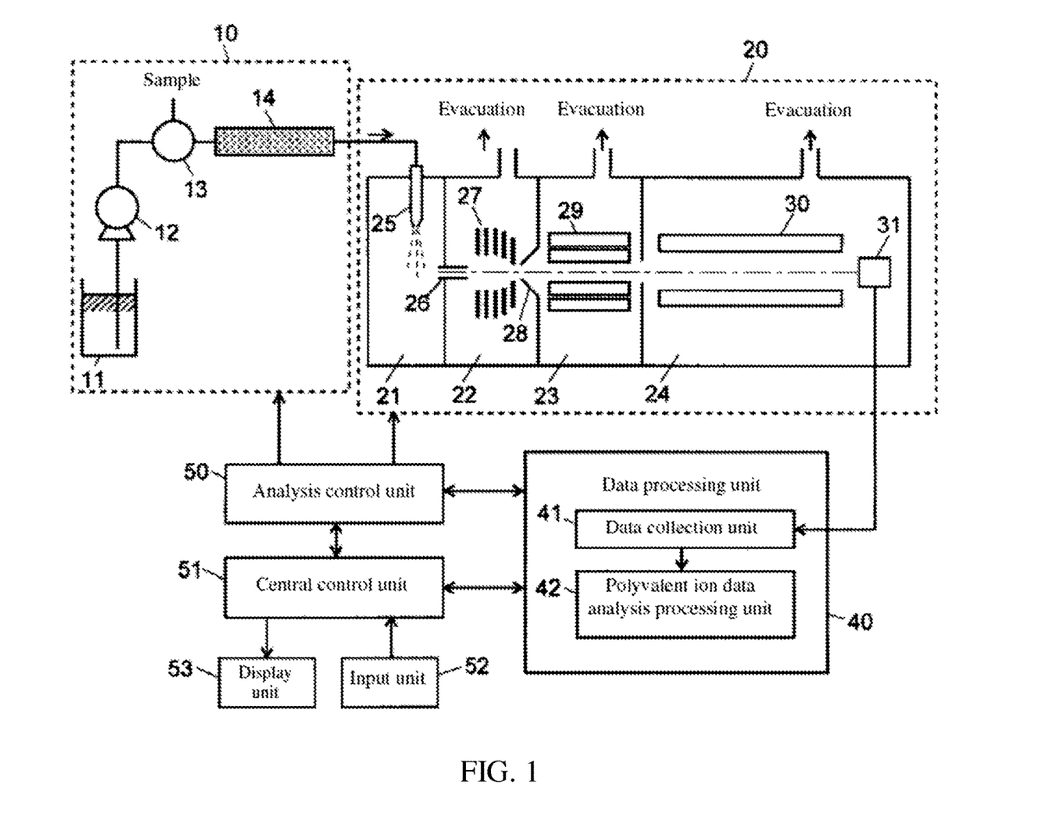
FIG. 1 Diagram of the main parts of an LC/MS constituting an example of embodiment of a chromatograph/mass spectrometer utilizing the data processing device of the present invention.

An example of embodiment of an LC/MS using the data processing device of the present invention will be described with reference to the appended drawings. FIG. 1 is a diagram of the main parts of the LC/MS of the present example of embodiment.

This LC/MS, broadly speaking, consists of a liquid chromatograph (LC) 10 and a mass spectrometry unit (MS) 20, and employs an electrospray ionization (ESI) interface for the atmospheric pressure ionization interface which connects the LC 10 to the MS 20.

In LC 10, a liquid feed pump 12 suctions a mobile phase stored in a mobile phase container 11 and feeds it at a fixed flow rate to column 14 via injector 13. When sample is injected into the mobile phase by means of an injector 13, the sample is carried by the flow of the mobile phase and is introduced into a column 14. While passing through the column 14, the compounds in the sample separate from each other and are eluted from the outlet of the column 14 at different times and introduced into the MS 20.

The MS 20 comprises an ionization chamber 21 which is maintained at an ambient pressure atmosphere and an analysis chamber 24 which is evacuated by a turbomolecular pump (not illustrated) and maintained at a high vacuum atmosphere, and between these, there is arranged a first intermediate vacuum chamber 22 and second intermediate vacuum chamber 23, which are maintained at stepwise higher degrees of vacuum. The ionization chamber 21 and first intermediate vacuum chamber 22 communicate via a narrow diameter desolventizing tube 26, and the first intermediate vacuum chamber 22 and second intermediate vacuum chamber 23 communicate via a small diameter orifice formed in the top part of a circular conical skimmer 28.

When eluate containing various compounds, supplied from LC 10 as the ion source, reaches the ESI nozzle 25, a direct current high voltage applied from an unillustrated high voltage power source causes an electric charge to be imparted to the eluate. The eluate is then sprayed in the form of charged microdrops into an ionization chamber 21. These charged drops collide with gas molecules of atmospheric origin and are broken down into smaller drops and quickly dry (are desolventized), whereby the sample molecules are gasified. The sample molecules are ionized in this process. Microdrops containing the generated ions are drawn into desolventizing tube 26 due to a pressure differential, and as they pass through the desolventizing tube 26, desolventizing progresses and ions are produced. When high molecular weight compounds such as proteins are ionized by ESI as described above, not only monovalent ions with a valence of 1, but also many polyvalent ions with a valence of 2 or more are generated.

Ions which have been generated in this manner pass through the two intermediate vacuum chambers 22, 23 while being focused by the respective ion guides 27, 29, and are fed into the analysis chamber 24. A quadrupole mass filter 30 and a detector 31 are arranged in the analysis chamber 24, and the quadrupole mass filter selectively allows through only those ions which have a particular mass-charge ratio among the various ions that are introduced. Ions which have passed through reach the detector 31 and are detected, and detector 31 outputs a current corresponding to the number of arriving ions as the detection signal. The mass-charge ratio of ions which pass through the quadrupole mass filter 30 depends on the voltage applied to the filter 30, so the mass-charge ratio of ions passing through the quadrupole mass filter 30 can be scanned by scanning this applied voltage over a predetermined range.

The detection signal generated by the detector 31 is inputted into data processing unit 40, and is first converted to digital data in data collection unit 41 and is temporarily stored in a storage device such as a memory. Multivalent ion data analysis processing unit 42 suitably reads data stored in the storage device in the data collection unit 41 and executes analysis processing to acquire information on the target compound constituting the object of analysis, as described later. Furthermore, analysis control unit 50 controls the operation of the various parts of LC 10 and MS 20 in order to execute LC/MS analysis based on instructions from central control unit 51.

Input unit 52 and display unit 53 are connected as user interfaces to central control unit 51, which receives user manipulations via input unit 52, outputs various instructions for analysis to analysis control unit 50 and data processing unit 40, and outputs the obtained analysis results to display unit 53. Some or most of the functions of the central control unit 51, analysis control unit 50 and data processing unit 40 can be implemented by executing predetermined control/processing software on a personal computer.

In the LC/MS described above, under control of the analysis control unit 50, from the time the sample is injected into the mobile phase by the injector 13 in the LC 10, scanning measurement is repeatedly executed across a predetermined mass-charge ratio range in MS 20. As a result, three-dimensional data having the three dimensions of time, mass-charge ratio m/z and signal intensity (ion intensity) is stored in the data collection unit 41. Polyvalent ion data analysis processing unit 42 executes the following distinctive processing on the data collected in this manner.

Figure 2:
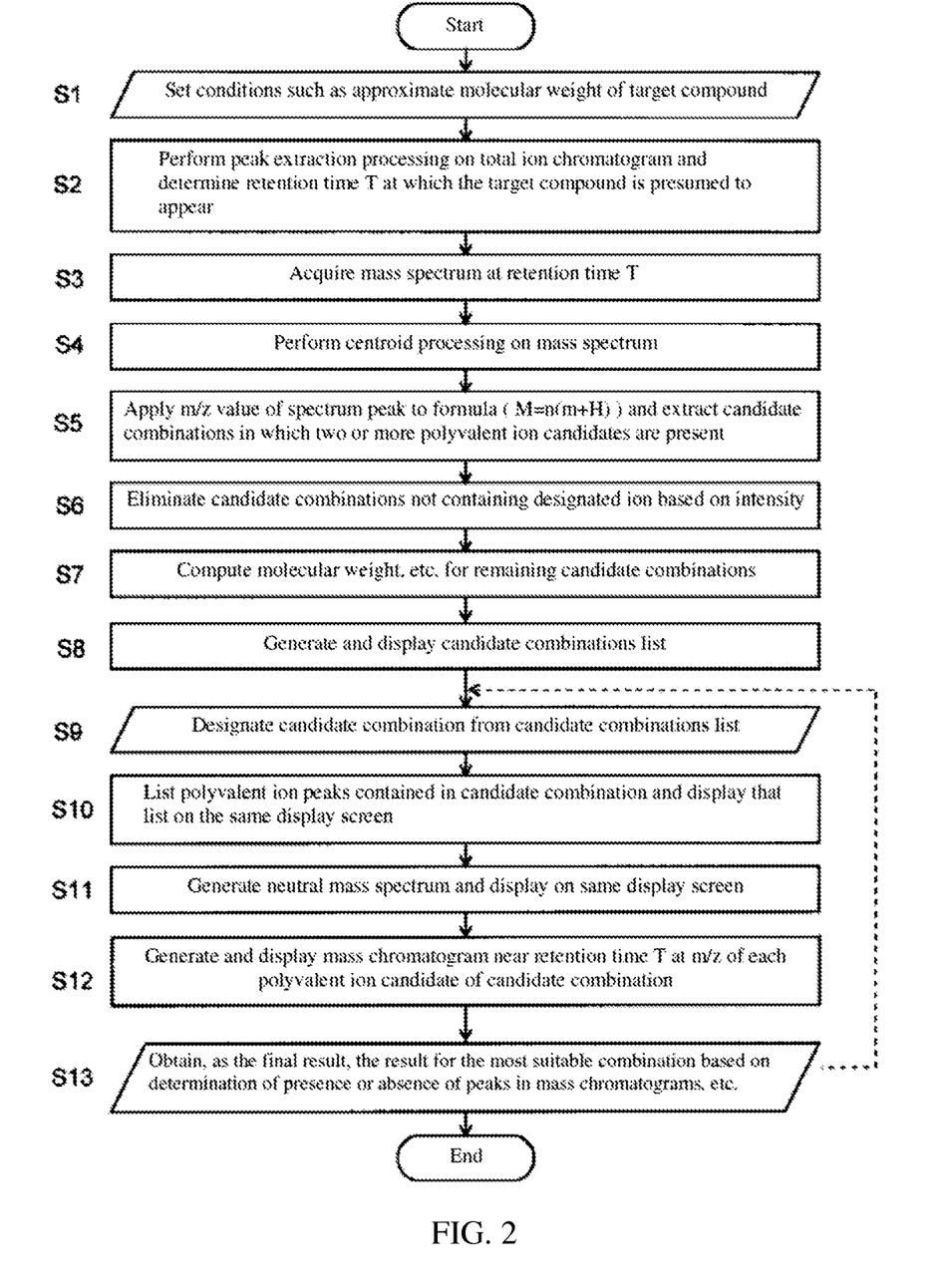
FIG. 2 A flow chart of polyvalent ion data processing in the LC/MS of the present example of embodiment.
Figure 3:
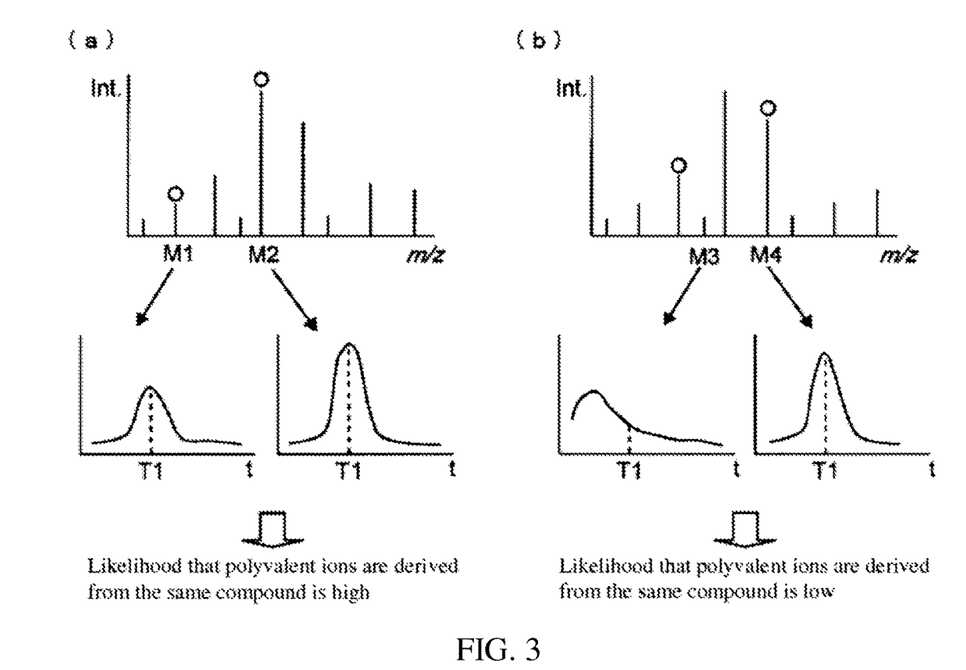
FIG. 3 An explanatory diagram of polyvalent ion data processing in the LC/MS of the present example of embodiment.
Figure 4:
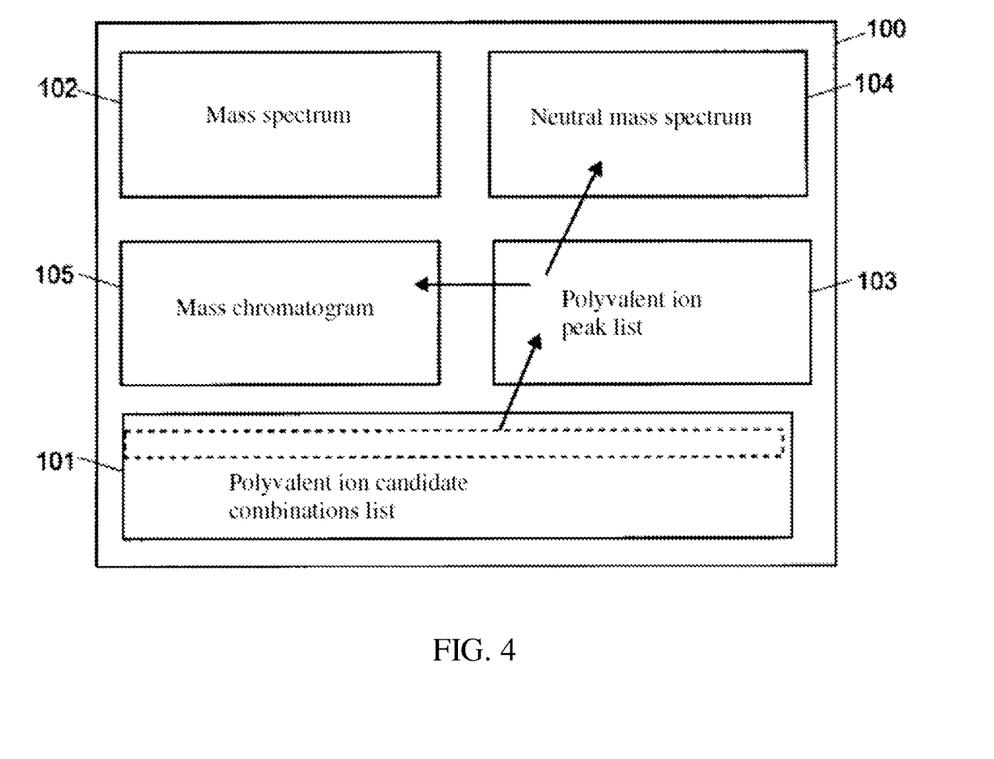
FIG. 4 An explanatory diagram of the screen displaying polyvalent ion data processing results in the LC/MS of the present example of embodiment.
Figure 5:
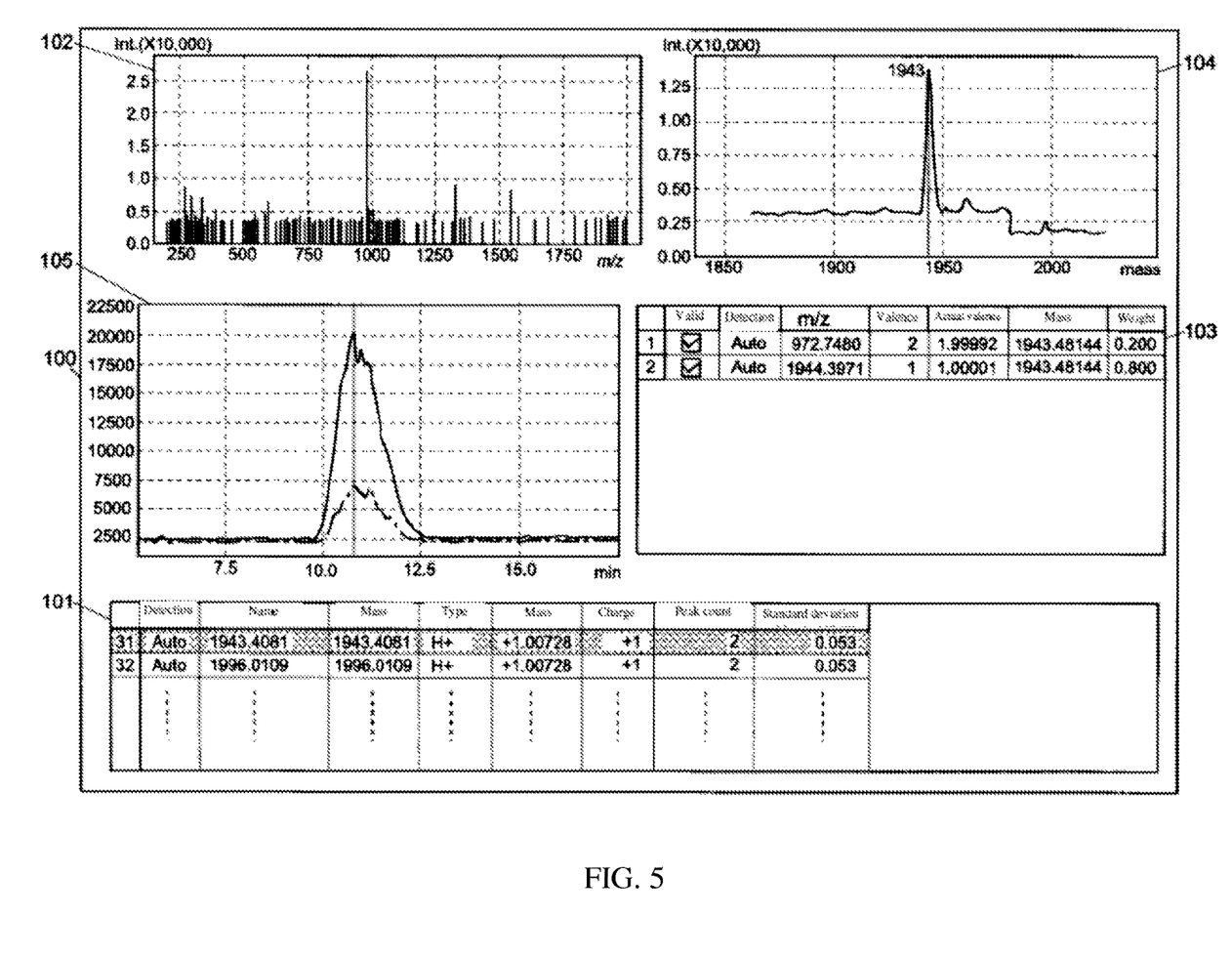
FIG. 5 A drawing illustrating an example of the display of polyvalent ion data processing results.

FIG. 2 is a flow chart of polyvalent ion data processing in the LC/MS of the present example of embodiment, FIG. 3 is an explanatory diagram of this polyvalent ion data processing, FIG. 4 is an explanatory diagram of the screen displaying polyvalent ion data processing results, and FIG. 5 is a drawing illustrating an example of the display of polyvalent ion data processing results.

Prior to execution of processing, the users inputs the retention time of the target compound, the estimated molecular weight of the target compound (or the approximate known molecular weight) or molecular weight range, the valence range of polyvalent ions generated from the target compound, the relative intensity threshold for polyvalent ion selection and the like as the parameters necessary for analysis, using the input unit 52 (step S1). The input of estimated molecular weight or molecular weight range and valence range is not essential, but inputting these makes it possible to reduce the number of candidate combinations, as described below, and reduces the effort of the work and operations performed by the user.

When the substantive analysis processing is initiated, the polyvalent ion data analysis processing unit 42 first generates a total ion chromatogram (or a base peak chromatogram with signal intensities of peaks with maximum signal intensity being arranged in the time direction in the mass spectrum for each time point) based on the collected data, extracts the peaks near the retention time of the target compound for that chromatogram, and computes the observed retention time T of the target compound from the time when the peak top of the peak appears (step S2). Next, mass spectrum data (profile data) is acquired at that retention time T (step S3), and centroid processing is performed on that profile data in order to generate a mass spectrum in which each peak is shown as a straight line (step S4). Prior to performing centroid processing, it is desirable to eliminate unnecessary peaks by executing baseline subtraction, smoothing or other noise removal processing.

Next, the peaks are extracted from the centroided mass spectrum and the mass-charge ratio m/z=m of each peak is determined. Furthermore, the mass-charge ratio m is applied to formula (1), reproduced below, and a combination of polyvalent ion peaks in which the mass-charge ratio m is present is extracted for each of two or more ion valences n for the same molecular weight as a candidate combination (step S5).

$$M=n(M+H) \tag{1}$$

In step S1, in the case where an estimated molecular weight M' has been given, the molecular weight M in formula (1) above is suitably limited to the range M'±ΔM (ΔM is suitably preset at one's discretion), and in the case where an estimated molecular weight range has been given, M in formula (1) above is suitably limited to the estimated molecular weight range. Furthermore, if neither an estimated molecular weight nor a molecular weight range has been given, M may be suitably limited using a preset default molecular weight range. Furthermore, if a valence range has been specified in step S1, n in the above formula (1) may be suitably limited to that valence range. Namely, the narrower the range of molecular weight M and the narrower the range of valence n in the above formula (1), the smaller will be the number of candidate combinations of polyvalent ion peaks which satisfy formula (1) above (in other words, candidates will be excluded because they do not match the conditions).

In cases where only polyvalent ion peaks derived from the target compound appear in the mass spectrum, only one candidate combination is extracted in step S5, which is the combination of true polyvalent ion peaks derived from the target compound. However, generally, peaks derived from various types of noise, peaks derived from other compounds or impurities which could not be adequately separated in LC 10, and the like, will also appear on the mass spectrum. Thus, if such peaks appear at a mass-charge ratio which satisfies formula (1) in respect of another molecular weight which is not the true molecular weight of the target compound, multiple candidate combinations including one or more false combinations will be extracted in step S5.

Thus, next, the polyvalent ion data analysis processing unit 42, in order to eliminate candidate combinations which contain only peaks with particularly low signal intensity, eliminates candidate combinations which do not contain even one peak with a signal intensity of high order (high order intensity peaks) (step S6). Specifically, the signal intensity of the peak (base peak) with the greatest signal intensity among the peaks appearing in the mass spectrum is determined, and this signal intensity is multiplied by the relative intensity threshold set in step S1 to determine the intensity threshold. Thus, this intensity threshold varies depending on the signal intensity of the base peak. Then peaks with a signal intensity at or above the aforementioned intensity threshold are extracted from among the peaks appearing in the mass spectrum, and such peaks can be treated as high order intensity peaks. In this case, the number of high order intensity peaks is indefinite, but in cases where there are too many peaks exhibiting an intensity at or above the intensity threshold, a predetermined number of peaks may be selected in descending order of signal intensity. Furthermore, a predetermined number of peaks may be selected in descending order of signal intensity from among all the peaks appearing in the mass spectrum, without performing peak selection based on an intensity threshold.

Then, for each remaining candidate combination from the selection in step S6, the molecular weight (neutral mass) of the target compound is computed based on the mass-charge ratio of the polyvalent ion peaks (candidates) (step S7), the candidate combinations are made into a list, and the generated list is displayed via central control unit 51 on the screen of the display unit 53 (step S8). In the example shown in FIG. 4, a candidate combination list display area 101 is provided at the bottommost part of the display screen 100, and the molecular weight, number of polyvalent ion peaks (peak count) contained, etc., as determined based on each candidate combination, are displayed in list format as shown in FIG. 5. A display area 102 for displaying the mass spectrum at retention time T is provided in the upper left part of the display screen 100. In FIG. 5, this display area 102 displays a centroided mass spectrum, but it is also possible to display profile data and a centroided mass spectrum in overlaid fashion.

The user views the candidate combinations list displayed on the display screen 100 of the display unit 53 described above, and designates, for example one of those candidate combinations using the input unit 52 (step S9). As shown in FIG. 5, the designated candidate combination is displayed in reverse video. Receiving the aforesaid designation, the polyvalent ion data analysis processing unit 42 acquires information such as the mass-charge ratio and valence of the polyvalent ion peak candidates contained in the designated candidate combination and generates a polyvalent ion peak list, and displays the generated list via the central control unit 51 in the polyvalent ion peak list display area 103 in the right middle part of the display screen 100 displayed on display unit 53 (step S10). Furthermore, the mass spectrum of the polyvalent ions listed in the polyvalent ion peak list is deconvoluted to determine the neutral mass spectrum, which is displayed in neutral mass spectrum display area 104 in the upper right part of the display screen 100 (step S11).

Furthermore, data in a predetermined time range near the retention time T for the mass-charge ratio of the polyvalent ion peaks listed in the polyvalent ion peak list is acquired from data collection unit 41, a mass chromatogram is generated for each polyvalent ion, and these are overlaid and displayed in mass chromatogram display area 105 at the middle left of the display screen 100 (step S12). In the display example of FIG. 5, there are only two polyvalent ions contained in the designated candidate combination, so two mass chromatograms are drawn in the mass chromatogram display area 105. Namely, when one candidate combination from the candidate combinations list is designated in step S9, the polyvalent ion peak list, neutral mass spectrum and mass chromatograms for the designated candidate combination are displayed on the same display screen 100. Displaying multiple mass chromatograms included in the candidate combination has the following significance.

The example of FIG. 3 (*a*) is a case where the mass-charge ratios of the polyvalent ions contained in the candidate combination are M1 and M2, and the example of FIG. 3 (*b*) is a case where the mass-charge ratios of the polyvalent ions contained in the candidate combination are M3 and M4. If the candidate combination shown in FIG. 3 (*a*) has been designated, mass chromatograms near retention time T=T1 for mass-charge ratios M1 and M2 are generated and displayed. Polyvalent ions of different valences derived from the same compound will differ in terms of signal intensity itself, but in the mass chromatogram, the peak tops thereof should all appear at retention time T1, and the peaks should have similar shape. FIG. 3 (*a*) is this sort of example, where in the two chromatograms, the peak tops appear at retention time T1 and the peak shapes are similar. If one can confirm that the mass chromatograms are in such a state, one can surmise that there is a high likelihood that the corresponding polyvalent ions are derived from the same target compound.

By contrast, in a case where the polyvalent ion peak candidates contained in the candidate combination are actually not derived from the target compound or are due to noise, the peak top in the mass chromatogram may not appear at retention time T1 and the peak shape may be different. FIG. 3 (*b*) is an example of this, where in one of the two mass chromatograms at mass-charge ratios M3 and M4, a peak having a peak top at retention time T1 does not appear, and its peak shape is also clearly different. If one can confirm that the mass chromatograms are in such a state, one can surmise with a high likelihood that the polyvalent ion peak candidates are false peaks not derived from the target compound.

In cases where multiple candidate combinations are listed in the candidate combinations list, the user designates candidate combinations one at a time using the input unit 52. As the designation changes, the polyvalent ion peak list, neutral mass spectrum and mass chromatograms displayed on the display screen 100 are updated. The user checks the shapes and peak positions of the mass chromatograms drawn in the mass chromatogram display area 105. Based on the results of this, the user then confirms the most suitable combination to be the polyvalent ion peaks derived from the target compound, and the precise molecular weight and neutral mass spectrum of the target compound are obtained (step S13).

With the LC/MS of the present example of embodiment, as described above, it becomes possible to eliminate the effects of noise, impurities, other compounds inadequately separated by LC, and the like, to find the polyvalent ions derived from the target compound, and to determine a highly precise molecular weight and neutral mass spectrum, even in cases where there are few types of polyvalent ions generated from the compound, specifically, about two or three.

In the example of embodiment described above, the user himself performed the operation of selecting candidate combinations from the candidate combination list and the work of checking the peak top positions and peak shapes of the mass chromatograms, but it is also possible to automatically perform this sort of operation and work (processing) to finally extract the most appropriate candidate combination and then present it to the user. Specifically, it is possible to determine the peak top position to be valid if the peak top is present within a predetermined tolerance range in relation to the retention time T1 of the target compound. Furthermore, for example, to assess the similarity of peaks of multiple mass chromatograms, it is suitable to calculate the error between two peaks at each time point after normalizing the peak top height, and compute an index value for determining similarity based on the sum of such errors or the like.

It should be noted that the example of embodiment described above is no more than one example, and it is evident that any suitable alterations, modifications and additions made within the gist of the present invention are also included within the scope of patent claims of the present application.

DESCRIPTION OF REFERENCE SYMBOLS

10 . . . Liquid chromatograph (LC)
11 . . . Mobile phase container
12 . . . Liquid feed pump
13 . . . Injector
14 . . . Column
20 . . . Mass spectrometry unit (MS)
21 . . . Ionization chamber
22, 23 . . . Intermediate vacuum chamber
24 . . . Analysis chamber
25 . . . ESI nozzle
26 . . . Desolventizing tube
27, 29 . . . Ion guide
28 . . . Skimmer
30 . . . Quadrupole mass filter
31 . . . Detector
40 . . . Data processing unit
41 . . . Data collection unit
42 . . . Polyvalent ion data analysis processing unit
50 . . . Analysis control unit
51 . . . Central control unit
52 . . . Input unit
53 . . . Display unit
100 . . . Display screen
101 . . . Candidate combination list display area
102 . . . Observed mass spectrum display area
103 . . . Polyvalent ion peak list display area
104 . . . Neutral mass spectrum display area
105 . . . Mass chromatogram display area

What is claimed is:

1. A chromatograph/mass spectrometer device which analyzes and processes data on polyvalent ions derived from a target compound and captured by a chromatograph/mass spectrometer, said chromatograph/mass spectrometer device comprising:
   a) a chromatograph configured to separate compounds;
   b) a mass spectrometer configured to ionize the compounds and sort ionized compounds by mass-to-charge ratio;
   c) a polyvalent ion candidate extractor which finds a plurality of candidate polyvalent ion peak combinations derived from the target compound by extracting multiple polyvalent ion peak candidates of different valence surmised to be derived from the same compound on a mass spectrum obtained in a vicinity of a retention time of the target compound;

d) a mass chromatogram generator which generates a mass chromatogram at least in a time range in the vicinity of the retention time of said target compound for each of the multiple polyvalent ion peak candidates contained in each of the plurality of candidate combinations determined by said polyvalent ion candidate extractor; and e) a candidate determination unit which selects appropriate candidate combinations from the plurality of candidate combinations determined by said polyvalent ion candidate extractor by determining whether or not each polyvalent ion peak candidate is a polyvalent ion peak derived from the target compound by comparing:
   times at which peaks of each of the multiple polyvalent ion peak candidates appear, and
   shapes of the peaks of each of the multiple polyvalent ion peak candidates,
based on multiple mass chromatograms for multiple polyvalent ion peak candidates contained in one candidate combination, generated by said mass chromatogram generator.

2. The chromatograph/mass spectrometer device as described in claim 1,
   wherein said polyvalent ion candidate extractor discards or selects the candidate combination on the condition that it contains at least one peak with a relatively large signal intensity on the mass spectrum obtained in the vicinity of the retention time of the target compound.

3. A chromatograph/mass spectrometer method which analyzes and processes data on polyvalent ions derived from a target compound and captured by a chromatograph/mass spectrometer, the chromatograph/mass spectrometer method comprising:

a) operating a chromatograph to separate compounds;

b) operating a mass spectrometer to ionize the compounds and sort ionized compounds by mass-to-charge ratio;

c) finding a plurality of candidate polyvalent ion peak combinations derived from the target compound by extracting multiple polyvalent ion peak candidates of different valence surmised to be derived from the same compound on a mass spectrum obtained in a vicinity of a retention time of the target compound;

d) generating a mass chromatogram at least in a time range in the vicinity of the retention time of said target compound for each of the multiple polyvalent ion peak candidates contained in each of the plurality of candidate combinations determined by said polyvalent ion peak candidate extraction; and e) selecting at least one appropriate candidate combination for each of the plurality of candidate combinations determined by said polyvalent ion candidate extractor by determining whether or not each polyvalent ion peak candidate is a polyvalent ion peak derived from the target compound by comparing:
   times at which peaks of each of the multiple polyvalent ion peak candidates appear, and
   shapes of the peaks of each of the multiple polyvalent ion peak candidates,
based on multiple mass chromatograms for multiple polyvalent ion peak candidates contained in one candidate combination, generated by said mass chromatogram generation.

4. The chromatograph/mass spectrometer method as described in claim 3 further comprising:
   discarding or selecting the candidate combination on the condition that it contains at least one peak with a relatively large signal intensity on the mass spectrum obtained in the vicinity of the retention time of the target compound.

* * * * *